United States Patent
Guevremont et al.

(10) Patent No.: US 6,703,609 B2
(45) Date of Patent: Mar. 9, 2004

(54) TANDEM FAIMS/ION-TRAPPING APPARATUS AND METHOD

(75) Inventors: Roger Guevremont, Gloucester (CA); Randy Purves, Gloucester (CA); David Barnett, Orleans (CA)

(73) Assignee: National Research Council Canada, Ottawa (CA)

(*) Notice: Subject to any disclaimer, the term of this patent is extended or adjusted under 35 U.S.C. 154(b) by 0 days.

(21) Appl. No.: 10/221,624

(22) PCT Filed: Mar. 14, 2001

(86) PCT No.: PCT/CA01/00311

§ 371 (c)(1),
(2), (4) Date: Sep. 13, 2002

(87) PCT Pub. No.: WO01/69218

PCT Pub. Date: Sep. 20, 2001

(65) Prior Publication Data

US 2004/0004185 A9 Jan. 8, 2004

Related U.S. Application Data

(60) Provisional application No. 60/189,085, filed on Mar. 14, 2000.

(51) Int. Cl.[7] ............................................. H01J 49/26
(52) U.S. Cl. ........................................ 250/287; 250/292
(58) Field of Search ................................ 250/287, 286, 250/288, 292, 290

(56) References Cited

U.S. PATENT DOCUMENTS

| 5,248,875 A | * | 9/1993 | Douglas et al. | ............. 250/282 |
| 5,811,800 A | * | 9/1998 | Franzen et al. | ............. 250/288 |
| 6,124,592 A | * | 9/2000 | Spangler | ..................... 250/287 |
| 6,489,608 B1 | * | 12/2002 | Skilling | ....................... 250/281 |

OTHER PUBLICATIONS

Guevremont et al. "Atmospheric pressure ion focusing in a high–field asymmetric waveform ion mobility spectrometer", vol. 70, No. 2, Review of Scientific instruments, pp. 1–14, Feb. 1999.*

* cited by examiner

Primary Examiner—Kiet T. Nguyen
(74) Attorney, Agent, or Firm—Freedman & Associates (57) ABSTRACT

A method for selectively transmitting ions using a FAIMS device is disclosed. A first analyzer region is defined by a space between first and second spaced apart electrodes. A second analyser region is provided in operational communication with the first analyzer region. Ions are provided to the first analyzer region. The ions are coupled from the first analyser region to the second analyzer region. An asymmetric waveform is used to generate an electric field within the first analyser region and a compensation voltage is applied to prevent some ions from exiting the analyser region. Conditions are provided within the second analyzer region for effecting a second different separation of ions therein. Finally, the separated ions are trapped to accumulate ions within a trapping region thereof.

36 Claims, 6 Drawing Sheets

TANDEM FAIMS/ION-TRAPPING APPARATUS AND METHOD

This application claims the benefit of U.S. Provisional Application Ser. No. 60/189,085 filed Mar. 14, 2000.

FIELD OF THE INVENTION

The present invention relates to an apparatus and method for separating ions, more particularly the present invention relates to an apparatus and method for separating ions based on the ion focusing principles of high field asymmetric waveform ion mobility spectrometry (FAIMS).

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are gated into the drift tube and are subsequently separated in dependence upon differences in their drift velocity. The ion drift velocity is proportional to the electric field strength at low electric field strength, for example 200 V/cm, and the mobility, K, which is determined from experimentation, is independent of the applied electric field. Additionally, in IMS the ions travel through a bath gas that is at sufficiently high pressure such that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied field, and K becomes dependent upon the applied electric field. At high electric field strength, K is better represented by $K_h$, a non-constant high field mobility term. The dependence of $K_h$ on the applied electric field has been the basis for the development of high field asymmetric waveform ion mobility spectrometry (FAIMS), a tern used by the inventors throughout this disclosure, and also referred to as transverse field compensation ion mobility spectrometry, or field ion spectrometry. Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. FAIMS offers a new tool for atmospheric pressure gas-phase ion studies since it is the change in ion mobility, and not the absolute ion mobility, that is being monitored.

The principles of operation of FAIMS using flat plate electrodes have been described by I. A. Buryakov, E. V. Krylov, E. G. Nazarov and U.Kh. Rasulev in a paper published in the International Journal of Mass Spectrometry and Ion Processes; volume 128 (1993), pp. 143–148, the contents of which are herein incorporated by reference. The mobility of a given ion under the influence of an electric field is expressed by: $K_h=K(1+f(E))$, where $K_h$ is the mobility of an ion at high electrical field strength, K is the coefficient of ion mobility at low electric field strength and f(E) describes the functional dependence of the ion mobility on the electric field strength. Ions are classified into one of three broad categories on the basis of a change in ion mobility as a function of the strength of an applied electric field, specifically: the mobility of type A ions increases with increasing electric field strength; the mobility of type C ions decreases; and, the mobility of type B ions increases initially before decreasing at yet higher field strength. The separation of ions in FAIMS is based upon these changes in mobility at high electric field strength. Consider an ion, for example a type A ion, which is being carried by a gas stream between two spaced-apart parallel plate electrodes of a FAIMS device. The space between the plates defines an analyzer region in which the separation of ions occurs. The net motion of the ion between the plates-is the sum of a horizontal x-axis component due to the flowing stream of gas and a transverse y-axis component due to the electric field between the parallel plate electrodes. The term "net motion" refers to the overall translation that the ion, for instance said type A ion, experiences, even when this translational motion has a more rapid oscillation superimposed upon it. Often, a first plate is maintained at ground potential while the second plate has an asymmetric waveform, V(t), applied to it. The asymmetric waveform V(t) is composed of a repeating pattern including a high voltage component, $V_1$, lasting for a short period of time $t_2$ and a lower voltage component, $V_2$, of opposite polarity, lasting a longer period of time $t_1$. The waveform is synthesized such that the integrated voltage-time product, and thus the field-time product, applied to the plate during each complete cycle of the waveform is zero, for instance $V_1 t_2+V_2 t_1=0$; for example +2000 V for 10 $\mu$s followed by −1000 V for 20 $\mu$s. The peak voltage during the shorter, high voltage portion of the waveform is called the "dispersion voltage" or DV in this disclosure.

During the high voltage portion of the waveform, the electric field causes the ion to move with a transverse y-axis velocity component $v_1=K_h E_{high}$, where $E_{high}$ is the applied field, and $K_h$ is the high field ion mobility under ambient electric field, pressure and temperature conditions. The distance traveled is $d_1=v_1 t_2=K_h E_{high} t_2$, where $t_2$ is the time period of the applied high voltage. During the longer duration, opposite polarity, low voltage portion of the asymmetric waveform, the y-axis velocity component of the ion is $v_2=KE_{low}$, where K is the low field ion mobility under ambient pressure and temperature conditions. The distance traveled is $d_2=v_2 t_1=KE_{low} t_1$. Since the asymmetric waveform ensures that $(V_1 t_2)+(V_2 t_1)=0$, the field-time products $E_{high} t_2$ and $E_{low} t_1$ are equal in magnitude. Thus, if $K_h$ and K are identical, $d_1$ and $d_2$ are equal, and the ion is returned to its original position along the y-axis during the negative cycle of the waveform, as would be expected if both portions of the waveform were low voltage. If at $E_{high}$ the mobility $K_h>K$, the ion experiences a net displacement from its original position relative to the y-axis. For example, positive ions of type A travel farther during the positive portion of the waveform, for instance $d_1>d_2$, and the type A ion migrates away from the second plate. Similarly, positive ions of type C migrate towards the second plate.

If a positive ion of type A is migrating away from the second plate, a constant negative dc voltage can be applied to the second plate to reverse, or to "compensate" for, this transverse drift. This dc voltage, called the "compensation voltage" or CV in this disclosure, prevents the ion from migrating towards either the second or the first plate. If ions derived from two compounds respond differently to the applied high strength electric fields, the ratio of $K_h$ to $K$ may be different for each compound. Consequently, the magnitude of the CV necessary to prevent the drift of the ion toward either plate is also different for each compound. Thus, when a mixture including several species of ions is being analyzed by FAIMS, only one species of ion is selectively transmitted for a given combination of CV and DV. The remaining species of ions, for instance those ions that are other than selectively transmitted through FAIMS, drift towards one of the parallel plate electrodes of FAIMS and are neutralized. Of course, the speed at which the remaining species of ions move towards the electrodes of FAIMS depends upon the degree to which their high field mobility properties differ from those of the ions that are selectively transmitted under the prevailing conditions of CV and DV.

An instrument operating according to the FAIMS principle as described previously is an ion filter, capable of selective transmission of only those ions with the appropriate ratio of $K_h$ to $K$. In one type of experiment using FAIMS devices, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained. It is a significant limitation of early FAIMS devices, which used electrometer detectors, that the identity of peaks appearing in the CV spectrum are other than unambiguously confirmed solely on the basis of the CV of transmission of a species of ion. This limitation is due to the unpredictable, compound-specific dependence of $K_h$ on the electric field strength. In other words, a peak in the CV spectrum is easily assigned to a compound erroneously, since there is no way to predict or even to estimate in advance, for example from the structure of an ion, where that ion should appear in a CV spectrum. In other words, additional information is necessary in order to improve the likelihood of assigning correctly each of the peaks in the CV spectrum. For example, subsequent mass spectrometric analysis of the selectively transmitted ions greatly improves the accuracy of peak assignments of the CV spectrum.

In U.S. Pat. No. 5,420,424 which issued on May 30, 1995, B. L. Carnahan and A. S. Tarassove disclose an improved FAIMS electrode geometry in which the flat plates that are used to separate the ions are replaced with concentric cylinders, the contents of which are herein incorporated by reference. The concentric cylinder design has several advantages, including higher sensitivity compared to the flat plate configuration, as was discussed by R. W. Purves, R. Guevremont, S. Day, C. W. Pipich, and M. S. Matyjaszczyk in a paper published in Reviews of Scientific Instruments; volume 69 (1998), pp 4094–4105. The higher sensitivity of the cylindrical FAIMS is due to a two-dimensional atmospheric pressure ion focusing effect that occurs in the analyzer region between the concentric cylindrical electrodes. When no electrical voltages are applied to the cylinders, the radial distribution of ions should be approximately uniform across the FAIMS analyzer. During application of DV and CV, however, the radial distribution of ions is not uniform across the annular space of the FAIMS analyzer region. Advantageously, with the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of FAIMS is thereby improved as a result of this two-dimensional ion focusing effect.

The focussing of ions by the use of asymmetric waveforms has been discussed above. For completeness, the behavior of those ions that are not focussed within the analyzer region of a cylindrical geometry FAIMS is described here, briefly. As discussed previously, those ions having high field ion mobility properties that are other than suitable for focussing under a given set of DV, CV and geometric conditions will drift toward one or another wall of the FAIMS device. The rapidity with which these ions move towards the wall depends on the degree to which their $K_h/K$ ratio differs from that of the ion that is transmitted selectively under the prevailing conditions. At the very extreme, ions of completely the wrong property, for instance a type A ion versus a type C ion, are lost to the walls of the FAIMS device very rapidly.

The loss of ions in FAIMS devices should be considered one more way. If an ion of type A is focussed, for example at DV 2500 volts, CV -11 volts in a given geometry, it would seem reasonable to expect that the ion is also focussed if the polarity of DV and CV are reversed, for instance DV of -2500 volts and CV of +11 volts. This, however, is not observed and in fact the reversal of polarity in this manner creates a mirror image effect of the ion-focussing behavior of FAIMS. The result of such polarity reversal is that the ions are not focussed, but rather are extremely rapidly rejected from the device,. The mirror image of a focussing valley, is a hill-shaped potential surface. The ions slide to the center of the bottom of a focussing potential valley (2 or 3-dimensions), but slide off of the top of a hill-shaped surface, and hit the wall of an electrode. This is the reason for the existence, in the cylindrical geometry FAIMS, of the independent "modes" called 1 and 2. Such a FAIMS instrument is operated in one of four possible modes: P1, P2, N1, and N2. The "P" and "N" describe the ion polarity, positive (P) and negative (N). The waveform with positive DV, where DV describes the peak voltage of the high voltage portion of the asymmetric waveform yields spectra of type P1 and N2, whereas the reversed polarity negative DV, waveform yields P2 and N1. The discussion thus far has considered positive ions but, in general, the same principles apply to negative ions equally.

A further improvement to the cylindrical FAIMS design is realized by providing a curved surface terminus of the inner electrode. The curved surface terminus is continuous with the cylindrical shape of the inner electrode and is aligned co-axially with an ion-outlet orifice of the FAIMS analyzer region. The application of an asymmetric waveform to the inner electrode results in the normal ion-focussing behavior described above, except that the ion-focussing action extends around the generally spherically shaped terminus of the inner electrode. This means that the selectively transmitted ions cannot escape from the region around the terminus of the inner electrode. This only occurs if the voltages applied to the inner electrode are the appropriate combination of CV and DV as described in the discussion above relating to 2-dimensional focussing. If the CV and DV are suitable for the focussing of an ion in the FAIMS analyzer region, and the physical geometry of the inner surface of the outer electrode does not disturb this balance, the ions will collect within a three-dimensional region of space near the terminus. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focussing effect of the electric fields of the FAIMS mechanism. This is an example of a three-dimensional atmospheric pressure ion trap, as disclosed in a copending PCT application in the name of R. Guevremont and R. Purves, the contents of which are herein incorporated by reference.

Ion focusing and ion trapping requires electric fields that are other than constant in space, normally occurring in a geometrical configuration of FAIMS in which the electrodes are curved, and/or are not parallel to each other. For example, a non-constant in space electric field is created using electrodes that are cylinders or a part thereof; electrodes that are spheres or a part thereof; electrodes that are elliptical spheres or a part thereof; and, electrodes that are conical or a part thereof. Optionally, various combinations of these electrode shapes are used.

As discussed above, one previous limitation of the cylindrical FAIMS technology is that the identity of the peaks appearing in the CV spectra are not unambiguously confirmed due to the unpredictable changes in $K_h$ at high electric field strengths. Thus, one way to extend the capability of instruments based on the FAIMS concept is to provide a way to determine the make-up of the CV spectra more accurately, such as by introducing ions from the FAIMS device into a mass spectrometer for mass-to-charge (m/z) analysis. Advantageously, the ion focusing property of cylindrical FAIMS devices acts to enhance the efficiency for transporting ions from the analyzer region of a FAIMS device into an external sampling orifice, for instance an inlet of a mass spectrometer. This improved efficiency of transporting ions into the inlet of the mass spectrometer is optionally maximized by using a 3-dimensional trapping version of FAIMS operated in nearly trapping conditions. Under near-trapping conditions, the ions that have accumulated in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a small orifice leading into the vacuum system of a mass spectrometer.

Additionally, the resolution of a FAIMS device is defined in terms of the extent to which ions having similar mobility properties as a function of electric field strength are separated tinder a set of predetermined operating conditions. Thus, a high-resolution FAIMS device transmits selectively a relatively small range of different ion species having similar mobility properties, whereas a low-resolution FAIMS device transmits selectively a relatively large range of different ion species having similar mobility properties. The resolution of FAIMS in a cylindrical geometry FAIMS is compromised relative to the resolution in a parallel plate geometry FAIMS because the cylindrical geometry FAIMS has the capability of focusing ions. This focusing action means that ions of a wider range of mobility characteristics are simultaneously focused in the analyzer region of the cylindrical geometry FAIMS. A cylindrical geometry FAIMS with narrow electrodes has the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means that the resolution of FAIMS increases as the radii of the electrodes are increased, with parallel plate geometry FAIMS having the maximum attainable resolution.

Note that, while the above discussion refers to the ions as being "captured" or "trapped", in fact, the ions are subject to continuous 'diffusion'. Diffusion always acts contrary to focussing and trapping. The ions always require an electrical, or gas flow force to reverse the process of diffusion. Thus, although the ions are focused into an imaginary cylindrical zone in space with almost zero thickness, or within a 3-dimensional ion trap, in reality it is well known that the ions are actually dispersed in the vicinity of this idealized zone in space because of diffusion. This is important, and should be recognized as a global feature superimposed upon all of the ion motions discussed in this disclosure. This means that, for example, a 3-dimensional ion trap actually has real spatial width, and ions continuously leak from the 3-dimensional ion trap, for several physical, and chemical reasons. Of course, the ions occupy a smaller physical region of space if the trapping potential well is deeper.

It is significant limitation of the prior art FAIMS device that, when operated in a mode for trapping ions within a 3-dimensional region of space, there is a finite loading of the trap that can be achieved. Ions in excess of the loading limit begin to spill out of the trapping fields and will be lost. This limitation of the prior art FAIMS device is particularly problematic in those cases when several ion species have appropriate mobility properties to be trapped during a same overlapping period of time. In other words, the number of analyte ions in the trap is smaller, due to the presence of trapped background ions, which reduces the instrument sensitivity and increases the detection limit of the analyte ions.

Of course, other apparatus for trapping ions are known in the prior art. For instance, one type of an ion trap mass spectrometer is an radio-frequency (rf) quadrupole ion trap (ITMS), a device operating at low pressure, with the capability of trapping ions for storage. This device is optionally used as a mass analyzer, by electrically causing the ions within the trap to successively, as a function of their mass-to-charge ratio (m/z), become unstable and be ejected from the trap. Despite the versatility of the ITMS, it also has a very significant limitation. Since the strength of the trapping forces inside the ITMS is limited, if the trap contains a large number of ions, the space-charge ion—ion repulsion forces will overcome the trapping action, and the ions will be lost. This limitation is most severe if a minor component is to be detected in the presence of large numbers of ions that are other than of particular interest. Other types of ion trap mass spectrometers include, but are not limited to Fourier Transform Ion Cyclotron Resonance (FT-ICR) mass spectrometers and Penning ion trap mass spectrometers.

In a typical experiment, the compounds of a sample are ionized inside of the ITMS using an electron beam ionizer, for example. Since this form of ionization is not compound selective, ions from many of the components of the sample are formed. If the sample is composed of some compounds in high concentration, and a compound of interest is at trace levels, then the ratio of the number of background ions relative to the analyte compound is very high. The space-charge effects in the ITMS are usually experimentally minimized by reducing the ionization time, and hence the total number of ions which must reside in the ITMS. Of course, this works very well, but unfortunately the ITMS suffers from a loss of sensitivity if this approach is used. If the ionization time is shortened the ratio of background ions to the analyte ions is not altered, but the numbers of both of these ions is simply reduced. The net result is that the signal for the compound of interest is decreased. Normally therefore, the detection limit for the compound of interest is increased as the number of the ions of interest decreases.

It would be advantageous to provide a method and an apparatus for selectively transmitting an analyte ion prior to their introduction into an ion trapping device, for example one of an ion trapping FAIMS and an ITMS. Advantageously, pre-separating the analyte ion from the background ions greatly increases the dynamic sensitivity range of ion trapping devices.

OBJECT OF THE INVENTION

In order to overcome these and other limitations of the prior art, it is an object of the present invention to provide an apparatus for separating ions having a relatively increased sensitivity toward a predetermined analyte ion.

In order to overcome these and other limitations of the prior art, it is an object of the present invention to provide an apparatus for separating ions in which ions that are other than of interest are selectively rejected within a first analyzer region of a tandem arrangement including two analyzers.

SUMMARY OF THE INVENTION

In accordance with the invention there is provided a method for trapping ions comprising the steps of:

a) providing a first analyzer region defined by a space between first and second spaced apart electrodes, the first analyzer region being in communication with a first ion inlet and a first ion outlet, the first ion inlet for receiving ions for introduction into the first analyzer region, the first ion outlet for providing ions from the first analyzer region;

b) providing a first asymmetric waveform and a first direct-current compensation voltage, to at least one of the first and second electrodes, to form an electric field therebetween, the first asymmetric waveform for effecting a difference in net displacement between the ions in the time of one cycle of the applied first asymmetric waveform;

c) setting the first compensation voltage for effecting a first separation of the ions to selectively transmit a first subset of the ions within the first analyzer region;

d) providing ions to the first analyzer region;

e) coupling ions from the ion outlet of the first analyzer region to a second analyzer; and, f) trapping the selectively transmitted second subset of the ions with the second analyzer to accumulate ions within a trapping region thereof.

In accordance with the invention there is provided an apparatus for trapping ions comprising:

a) a first analyzer comprising at least two spaced apart electrodes defining a first analyzer region therebetween;

b) an ion source for providing ions to the first analyzer region;

c) a voltage source for providing an asymmetric waveform and a direct-current compensation voltage to at least one of the two electrodes of the first analyzer, to form an electric field therebetween, the asymmetric waveform for in use effecting a difference in net displacement between the ions in the time of one cycle of the applied asymmetric waveform and the compensation voltage for, in use, effecting a first separation of the ions by selectively transmitting a first subset of the ions within the first analyzer region;

d) a second analyzer for trapping ions, the second analyzer comprising at least two spaced apart electrodes defining a second analyzer region therebetween, the second analyzer region in fluid communication with the first analyzer region for in use receiving ions from the first analyzer region; and, e) a voltage source for providing at least a temporally varying voltage to at least one of the two electrodes of the second analyzer, to form an electric field therebetween, the electric field for in use trapping ions from the first subset of the ions within the second analyzer region;

wherein in use the ion source is operated for a longer continuous period of time relative to an operation of a same ion source interfaced to an apparatus having a single analyzer.

BRIEF DESCRIPTION OF THE DRAWINGS

FIG. 3a is a schematic diagram showing an ensemble of ions within a potential well of a prior art ion-trapping device;

FIG. 3b shows a hypothetical detector response following the detection of the trapped ions shown in FIG. 3a;

FIG. 4b shows a hypothetical detector response following the detection of the trapped ions shown in FIG. 4a;

FIG. 5a is a schematic diagram showing an ensemble of ions within a potential well of an ion-trapping device according to the present invention, the ions produced during a relatively longer ionization period than for FIG. 4a;

FIG. 5b shows a hypothetical detector response following the detection of the trapped ions shown in FIG. 5a;

DETAILED DESCRIPTION OF THE INVENTION

Figure 1:
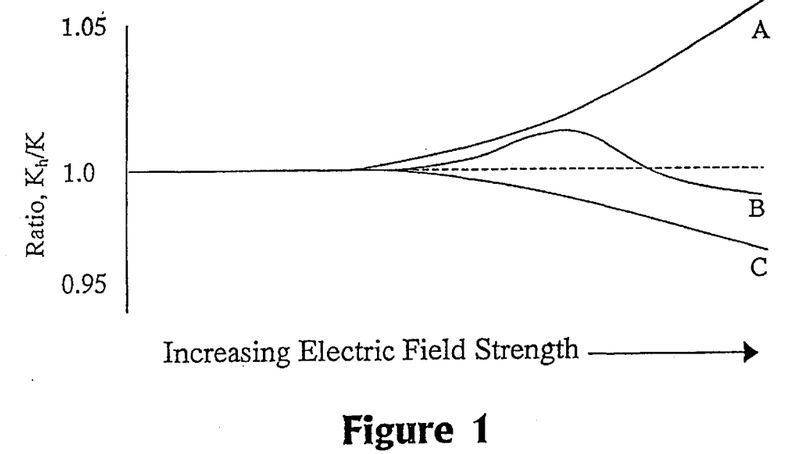
FIG. 1 shows three possible examples of changes in ion mobility as a function of the strength of an electric field.

Referring to FIG. 1, shown are three possible examples of the change in ion mobility properties with increasing electric field strength, as was discussed previously. The separation of ions in FAIMS is based upon a difference in these mobility properties for a first ion relative to a second ion. For instance, a first type A ion having a low field mobility $K_{1,low}$ is not separated in a FAIMS device from a second type A ion having a second different low field mobility $K_{2,low}$, if under the influence of high electric field strength, the ratio $K_{1,high}/K_{1,low}$ is equal to the ratio $K_{2,high}/K_{2,low}$. Interestingly, however, this same separation is achieved using conventional ion mobility spectrometry, which is based on a difference in ion mobilities at low applied electric field strength.

Figure 2A:
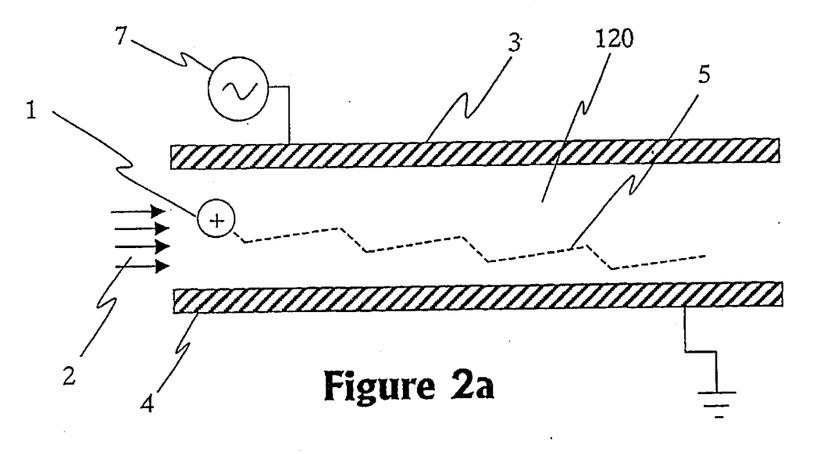
FIG. 2a illustrates the trajectory of an ion between two parallel plate electrodes under the influence of the electrical potential V(t)
Figure 2B:
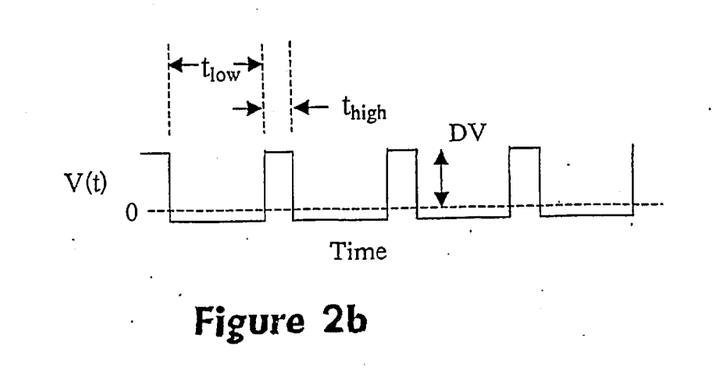
FIG. 2b shows an asymmetric waveform described by V(t)

Referring to FIG. 2a, shown is a schematic diagram illustrating the mechanism of ion separation according to the FAIMS principle. An ion 1, for instance a positively charged type A ion, is carried by a gas stream 2 flowing between two spaced apart parallel plate electrodes 3 and 4. One of the plates 4 is maintained at ground potential, while the other plate 3 has an asymmetric waveform described by V(t), applied to it. The peak voltage applied during the waveform is called the dispersion voltage (DV), as is shown in FIG. 2b. Referring still to FIG. 2b, the waveform is synthesized so that the electric fields during the two periods of time $t_{high}$ and $t_{low}$ are not equal. If $K_h$ and K are identical at high and low fields, the ion 1 is returned to its original position at the end of one cycle of the waveform. However, under conditions of sufficiently high electric fields, $K_h$ is greater than K and the distances traveled during $t_{high}$ and $t_{low}$ are no longer identical. Within an analyzer region defined by a space 120 between the first and second spaced apart electrode plates, 3 and 4, respectively, the ion 1 experiences a net displacement from its original position relative to the plates 3 and 4, as illustrated by the dashed line 5 in FIG. 2a.

If a type A ion is migrating away from the upper plate 3, a constant negative dc compensation voltage CV is applied to plate 3 to reverse or "compensate" for this offset drift. Thus, the ion 1 does not travel toward either plate. If two species of ions respond differently to the applied high electric field, for instance the ratios of $K_h$ to K are not identical, the compensation voltages necessary to prevent their drift toward either plate are similarly different. To analyze a mixture of ions, the compensation voltage is, for example, scanned to transmit each of the components of a mixture in turn. This produces a compensation voltage spectrum, or CV spectrum.

Figures 3A, 3B:
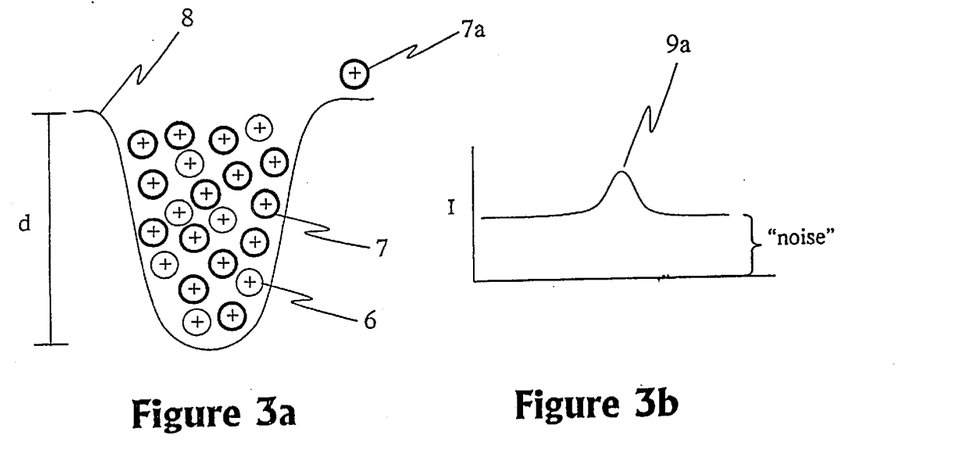

Referring to FIGS. 3a and 3b, shown is a schematic description of a mode of operation of an ion trapping device, for instance one of an rf quadrupole ion trap and an ion trapping FAIMS device, according to the prior art. In FIG. 3a the analyte ions 6, are present as a minor component, the analyte ions 6 being substantially diluted by the larger number of background ions 7. Both species of ions 6 and 7 are trapped within the potential well 8 that is created by the application of appropriate electric fields and/or gas flows through the ion trapping devices. The strength of the trapping forces inside the ion trapping device is limited, such that the potential well has a maximum depth 'd', as illustrated in FIG. 3a. In other words, there is always a finite loading of the trap that can be achieved. Ions in excess of the loading limit, for instance ion 7a, begin to spill out of the trapping fields and will be lost. The ion trapping device producing the potential well shown schematically in FIG. 3a is therefore fully loaded. Shown in FIG. 3b is a hypothetical detector response showing the intensity of the analyte ions extracted from the potential well 8 of the trap, with reference to FIG. 3a, as a function of some instrumental parameter, for instance CV in an ion trapping FAIMS and mass-to-charge ratio in an rf quadrupole ion trap. The analyte signal 9a, though certainly discernable, is other than maximized relative to the 'noise', wherein the noise includes contributions from each of the instrument electronics and the presence of background ions.

Figure 4A:
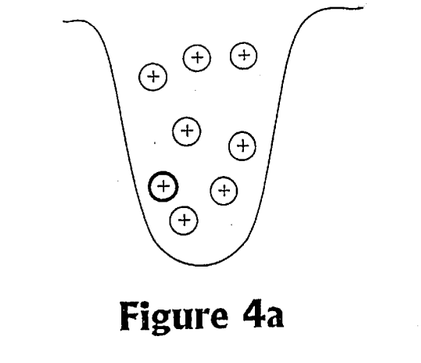
FIG. 4a is a schematic diagram showing an ensemble of ions within a potential well of an ion-trapping device according to the present invention, the ions produced during a relatively brief ionization period.
Figures 4B, 5B:
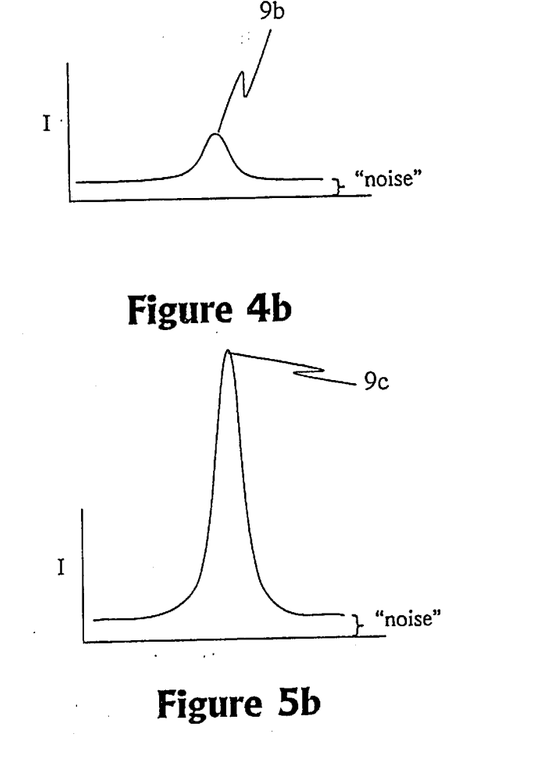

Referring to FIGS. 4a and 4b, shown is a schematic description of a mode of operation of an ion-trapping device, for instance one of an rf quadrupole ion trap and an ion-trapping FAIMS device, that is operationally interfaced to a FAIMS filter according to the present invention. The FAIMS filter is disposed within the ion path between an ionization source and the ion-trapping device, the FAIMS filter for performing a pre-separation of the analyte ions from the background ions. The FAIMS filter, for instance a FAIMS device having an appropriate geometry, separates the ions that are provided by an ionization source on the basis of the FAIMS principle, such that only a desired analyte ion is selectively transmitted to the ion-trapping device. Then, for a same potential well depth that was discussed with reference to FIG. 3a, and under substantially similar experimental conditions, the number of analyte ions relative to the number of background ions is greatly enhanced. Shown in FIG. 4b is a hypothetical detector response illustrating the intensity of an analyte signal corresponding to ions extracted from the potential well 8 of the ion trap, with reference to FIG. 4a, as a function of some instrumental parameter, for instance CV in an ion trapping FAIMS and mass-to-charge ratio in an rf quadrupole ion trap. The analyte signal 9b is substantially enhanced relative to the 'noise', wherein the noise includes contributions from each of the instrument electronics and the presence of background ions, compared to analyte signal 9a that is shown in FIG. 3b.

Figure 5A:
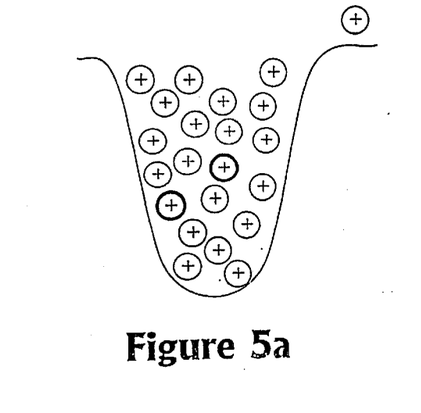

The inventors have realized, however, that additional and unforeseen advantages are realized by operationally interfacing a FAIMS filter to an ion-trapping device, such as for instance one of an rf quadrupole ion trap and an ion trapping FAIMS device. Referring to FIGS. 5a and 5b, shown is a schematic description of another mode of operation of an ion-trapping device, for instance one of an rf quadrupole ion trap and an ion trapping FAIMS device, that is operationally interfaced to a FAIMS filter according to the present invention. The FAIMS filter is disposed between an ionization source and the ion-trapping device, the FAIMS filter for performing a pre-separation of the analyte ions from the background ions. The FAIMS filter, for instance a FAIMS device having an appropriate geometry, separates the ions that are provided by an ionization source on the basis of the FAIMS principle, such that only a desired analyte ion is selectively transmitted to the ion-trapping device. As previously discussed, a signal-to-noise advantage is realized by preventing the background ions from entering the ion-trapping device, as was discussed with reference to FIGS. 4a and 4b.

Unfortunately, as shown in FIG. 4a, the ion-trapping device is other than fully loaded when the prevailing experimental conditions are substantially similar those that were used absent the FAIMS filter. Referring again to FIG. 5a, an additional advantage is realized by extending the duration of sample ionization, which provides additional analyte ions for storage in the ion-trapping device. Of course, the number of background ions being produced by the ionization source is also increased proportionately. Advantageously, the number of analyte ions within the trapping potential well is increased in absolute terms. As shown in FIG. 5b, the analyte signal 9c is effectively maximized relative to the 'noise', wherein the noise includes contributions from each of the instrument electronics and the presence of background ions. Operation of the FAIMS filter/ion-trapping device according to the present invention described with reference to FIGS. 5a and 5b yields the lowest detection limits and highest sensitivity for detection of analyte species by mass spectral analysis. As was previously discussed, the same degree of sensitivity enhancement is other than possible for mass spectral analyzers operating in a continuous mode.

Figure 6:
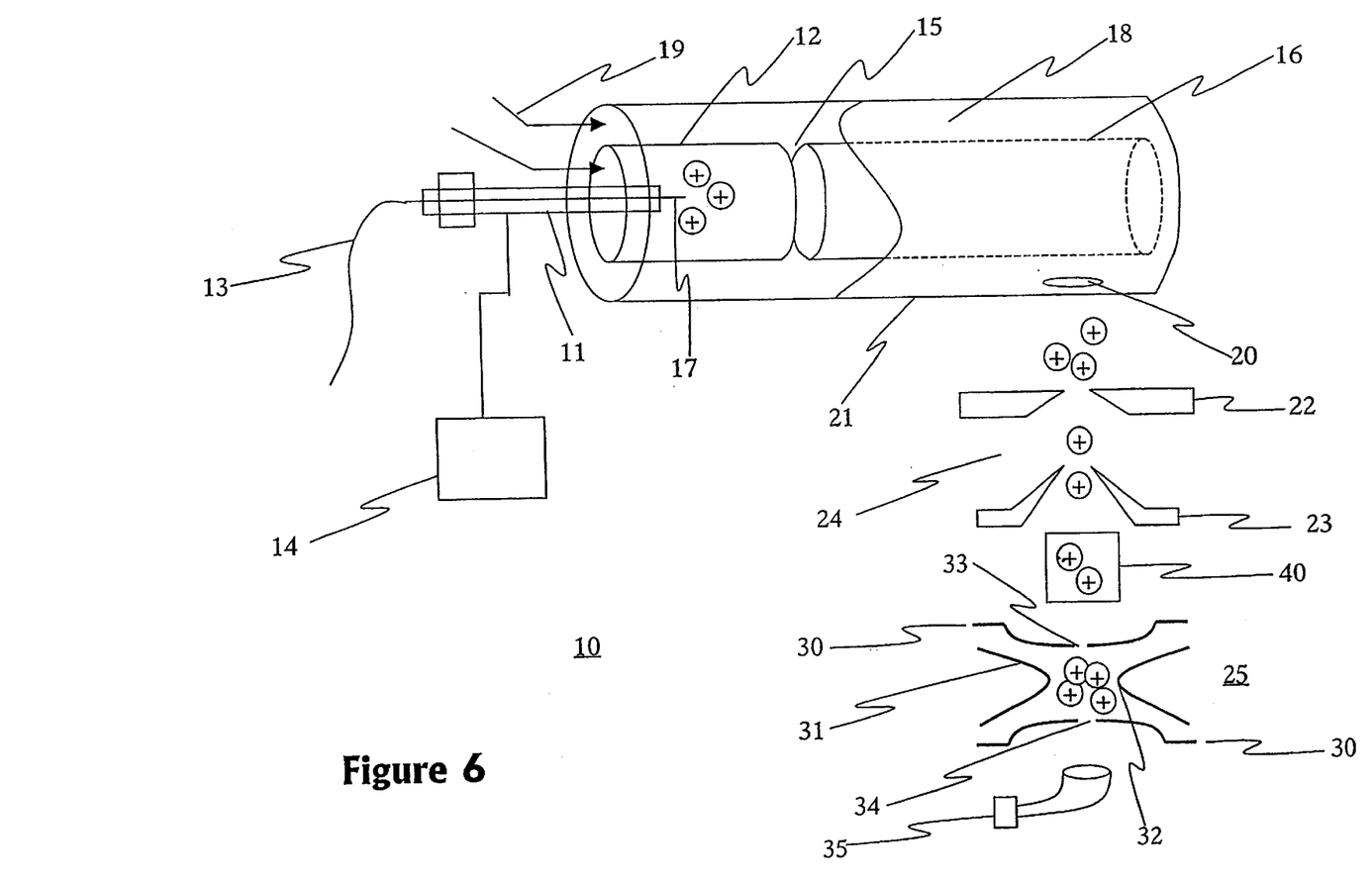
FIG. 6 shows an apparatus according to a first preferred embodiment of the present invention.

Referring to FIG. 6, a tandem FAIMS-ITMS according to a first preferred embodiment of the present invention is shown generally at 10. The ions are produced, for example, by electrospray ionization at a needle 11 held within the short inner cylinder 12 of FAIMS. The system for delivery of a sample through capillary 13, and the high voltage power supply 14 needed to create the strong electric fields for ionization, are shown in simplified form in FIG. 6. Under the influence of the electric fields around the tip of the electrospray needle 17, the ions move radially outward through the gap 15 between the short cylinder 12 and the long inner FAIMS electrode 16. An inward flow of gas through the gap 15 serves to act as a curtain gas and helps to desolvate the ions, and to prevent neutral compounds, and droplets from entering the FAIMS analyzer region 18. The ions are carried along the length of said analyzer region 18 by the carrier gas flow 19. The ions exit FAIMS through a port 20 in the outer FAIMS electrode 21. The ions are separated in the analyzer region 18 by application of a high voltage asymmetric waveform and a low voltage dc compensation voltage to the inner electrode 16. The waveform and compensation voltage establish conditions that are suitable for transmission of only the ions that have the appropriate ratio of mobility at low and high electric fields. Of course, another different species of ion is selected by altering the values of these two voltages.

Still referring to FIG. 6, the ions exit FAIMS through orifice 20, and move towards the orifice plate 22 under the influence of gas flows and/or electric fields between the outer electrode 21 of FAIMS and said orifice plate 22. The ions pass into the low pressure, vacuum chamber of the mass spectrometer through a differentially pumped interface composed of the orifice plate 22, a skimmer cone 23 and the gap 24 between said plate 22 and skimmer 23 which is pumped to low pressure by a mechanical roughing pump (not shown). Optional ion guide optics 40 help to move the ions from the skimmer cone to the ion trap apparatus 25. The ion trap is typically composed of two end cap electrodes 30, and a surrounding doughnut shaped ring electrode 31 having hyperbolic curved inner surface 32. The end cap electrodes 30 typically have one or more orifices 33 and 34 that serve to permit ions to enter and leave the ion trap. A detector 35 is mounted adjacent to the orifice 34 in one of the end caps 30. The details of the mechanical and electrical connections to the ion trap 25, the electronics necessary for operation, the plumbing for gas flows, and vacuum pumping are well known, and are not shown in FIG. 6.

In conventional ESI-IT configuration, the electrospray ionization source would be located near the orifice plate 22, in conjunction with a means for removal of solvent vapors and for desolvation of the ions, including a curtain gas approach used in some commercial mass spectrometers. In this configuration, all species of ions that are formed by the electrospray source are sampled by the mass spectrometer, and if there is an abundance of background ions, the ion trap will not have good sensitivity for minor components in the sample. Using the present embodiment of the combined FAIMS-ITMS shown in FIG. 6, the FAIMS apparatus serves to minimize the number of background ions that enter the vacuum system, and to maximize the relative number of ions of the compound of interest. This is achieved by setting the dispersion voltage, and compensation voltages of FAIMS to selectively transmit the compound of interest. A further advantage, also a consequence of the discrete mode of operation of the ITMS, is that the ion trap can accept ions for relatively longer periods of time without a buildup of a significant space-charge. Additionally, a significantly higher proportion of analyte ions accumulates in the ITMS, relative to the background ions and relative to the number of analyte ions that are otherwise accepted during operation of the ITMS absent the FAIMS device.

The FAIMS-ITMS combination is optionally used to study structure-specific interactions/reactions between isobaric (same mass-to-charge (m/z) ratio ions) and isomeric (same ions with different arrangement of chemical bonds) ions, which cannot be separated by mass spectrometric techniques alone, and various reactant gases. For example, the FAIMS has been shown to separate protein conformers, for instance protein ions with the same m/z ratio, but with different 3-dimensional structure. Advantageously, by setting an appropriate CV value the FAIMS is used to select a desired conformer for one charge state of the protein, such that the desired conformer is selectively introduced into the ITMS. Other charge states that are also transmitted at this CV are ejected from the ion trap in dependence only upon m/z ratio. A small amount of reactant gas, for instance $D_2O$ to do hydrogen-deuterium (H/D) exchange experiments, is optionally added to the ion trap. The exchange rate of H and D is monitored as a function of reaction time, as determined from changes in the m/z values of the ions when the heavier deuterium atoms replace the lighter hydrogen atoms. This experiment is optionally repeated for the other conformers of the same charge state that are transmitted through FAIMS at different CV values. The rate of H/D exchange is a function of the 3-dimensional structures of the protein ions. Advantageously, using FAIMS to separate the conformers before they are transmitted into the ITMS permits a study of the properties of individual conformers, an experiment not possible with ITMS alone. These types of experiments provide valuable information related to the structures of these conformers. Further, the discrete mode of operation of the ion trap, which allows the ITMS to be used as a chemical reactor for ions whereby the ions are reacted with other species for variable periods of time, is a critical requirement for performing these experiments. In other words, it is other than possible to obtain these experimental data using any mass spectrometric techniques that are based on a continuous mode of operation.

Of course, prior art radio-frequency ion traps comprise complex circuitry and controllers for monitoring ion trap loading, and for adjusting an ionization period accordingly to avoid overloading the ion trap. The electronics for controlling ion trap loading are expensive and incur unnecessary delays during operation. It is therefore a further advantage of the present invention that the selective rejection of background ions within the first analyzer region significantly reduces the extent to which the ion trap is loaded. At the very least, reducing the total ion current arriving at the ion trap minimizes the period of time that the electronics for controlling ion trap loading must be active during an experiment. At an extreme, the present invention permits operation of the radio-frequency ion trap absent any electronics for controlling ion trap loading.

Figure 7:
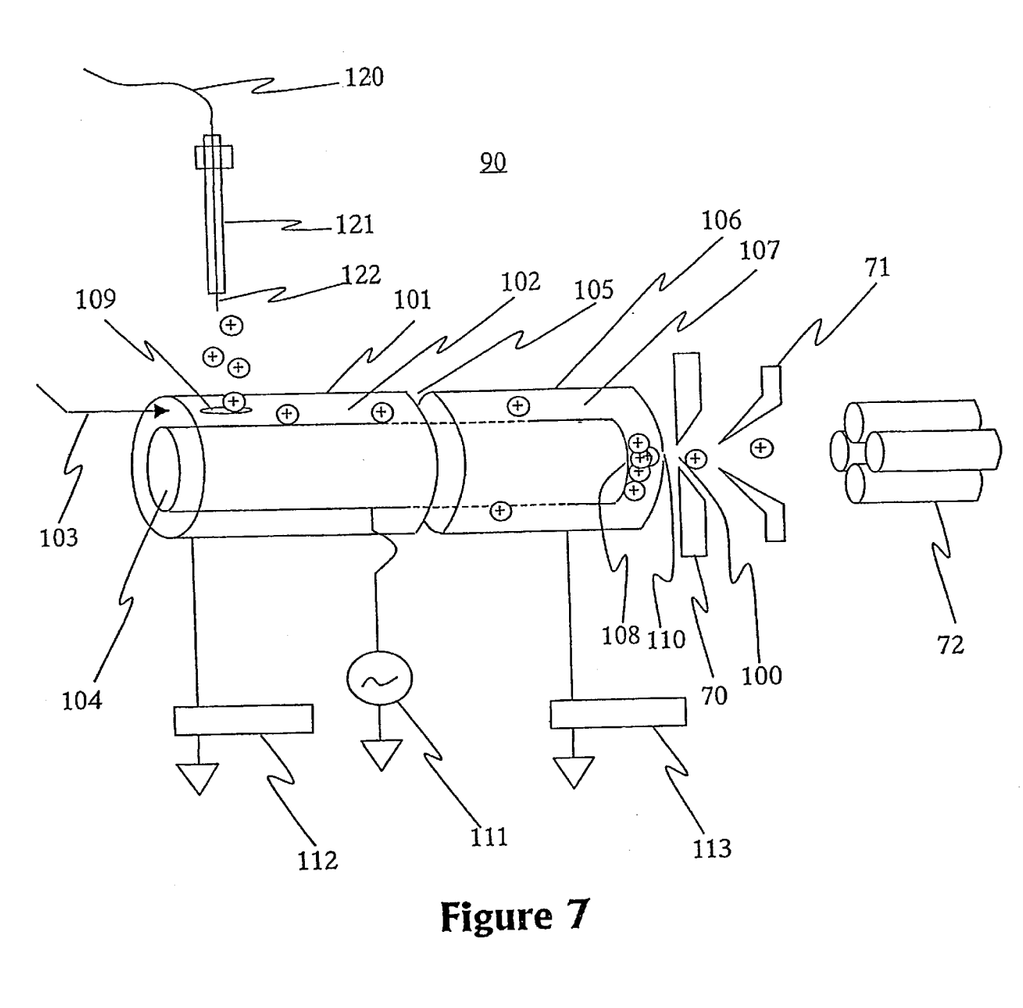
FIG. 7 shows an apparatus according to a second preferred embodiment of the present invention.

Referring to FIG. 7, a second preferred embodiment of the present invention comprising a tandem FAIMS/ion-trapping FAIMS device, is shown generally at 90. The ions are produced, for example, using a corona discharge ionization source with an electric connection 120 and a needle 121 with a fine tip 122 that is held at high voltage (power supply not shown). The ions that are generated by the electrospray ionization source move across the gap between the fine tip 17 and an orifice 109 in FAIMS outer electrode 101 leading into FAIMS 90, under the influence of the electric field generated by the high voltage applied to the needle 11. The ions are carried along the length of FAIMS in an analyzer region 102 by a carrier gas flow 103. Ions are separated in the analyzer region 102 because of the motion of the ions within this analyzer region induced by application of an asymmetric waveform and a dc compensation voltage, provided by electrical controller 111, to the inner FAIMS electrode 104 having a curved surface terminus 108. Only a subset of the original ions, for instance those ions having appropriate mobility properties, are selectively transmitted through the analyzer region 102 and reach the gap 105 between the FAIMS outer electrodes 101 and 106. Although not shown in FIG. 7, a gas flow optionally occurs into FAIMS or out of FAIMS at the gap 105. Further optionally the FAIMS outer electrodes 101 and 106 are held at different electrical voltages by independent power supplies 112 and 113, respectively, which effectively corresponds to application of different compensation voltages to the FAIMS defined by the outer electrodes 101 and 106. Consequently, different electric field conditions exist within the analyzer region 102 between electrode 104 and electrode 101 and the analyzer region 107 between electrode 104 and electrode 106. In other words, those ions that reach gap 105 are carried into the analyzer region 107, in which the electric field is optionally different than the electric field in analyzer region 102. Only a portion of the ions that reach gap 105 will have appropriate mobility properties to also pass through analyzer region 107.

Still referring to FIG. 7, the curved surface terminus 108 is continuous with the cylindrical shape of the FAIMS inner electrode 104 and is aligned co-axially with an ion-outlet orifice 110 of the FAIMS analyzer region 107. The application of an asymmetric waveform to the inner electrode 104 results in the normal ion-focussing behavior within analyzer region 107, except that the ion-focussing action extends around the generally spherically shaped terminus 108 of the inner electrode 104. This means that the selectively transmitted ions cannot escape from the region around the terminus 108 of the inner electrode 104. This will only occur if the voltages applied to the inner electrode 104 are the appropriate combination of CV and DV as described in the discussion above relating to 2-dimensional focussing. If the CV and DV are suitable for the focussing of an ion in the FAIMS analyzer region 107, and the physical geometry of the inner surface of the outer electrode does not disturb this balance, the ions will collect within a three-dimensional region of space near the terminus 108. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode will migrate back towards the inner electrode, due to the focusing action of the applied electric fields. When all forces acting upon the ions are balanced, the ions are effectively captured in every direction, either by forces of the flowing gas, or by the focussing effect of the electric fields of the FAIMS mechanism.

Advantageously, the flexibility to independently apply different combinations of DV and CV within analyzer regions 102 and 107 results in higher resolution for ion separations performed using apparatus 90. For example, an ion of interest is selectively transmitted through FAIMS under each of a plurality of different appropriate combinations of DV and CV. Thus, by applying a first appropriate combination of DV and CV between the electrodes defining a first analyzer region, the ion of interest is separated from ions that are other than of interest, for example background ions having mobility properties differing from the mobility properties of the ion of interest by more than a first threshold value. Of course, the first separation selectively transmits a subset of the original ions, including the ion of interest and those background ions that have mobility properties differing from the mobility properties of the ion of interest by less than the first threshold value. By applying a second appropriate combination of DV and CV between the electrodes defining a second analyzer region, however, the ion of interest is further separated from the remaining background ions, for example from those background ions having mobility properties differing from the mobility properties of the ion of interest by more than a second threshold value. Of course, background ions having mobility properties differing from the mobility properties of the ion of interest by less than the second threshold value are also transmitted through orifice 70 and into mass spectrometer 72.

Figure 8:
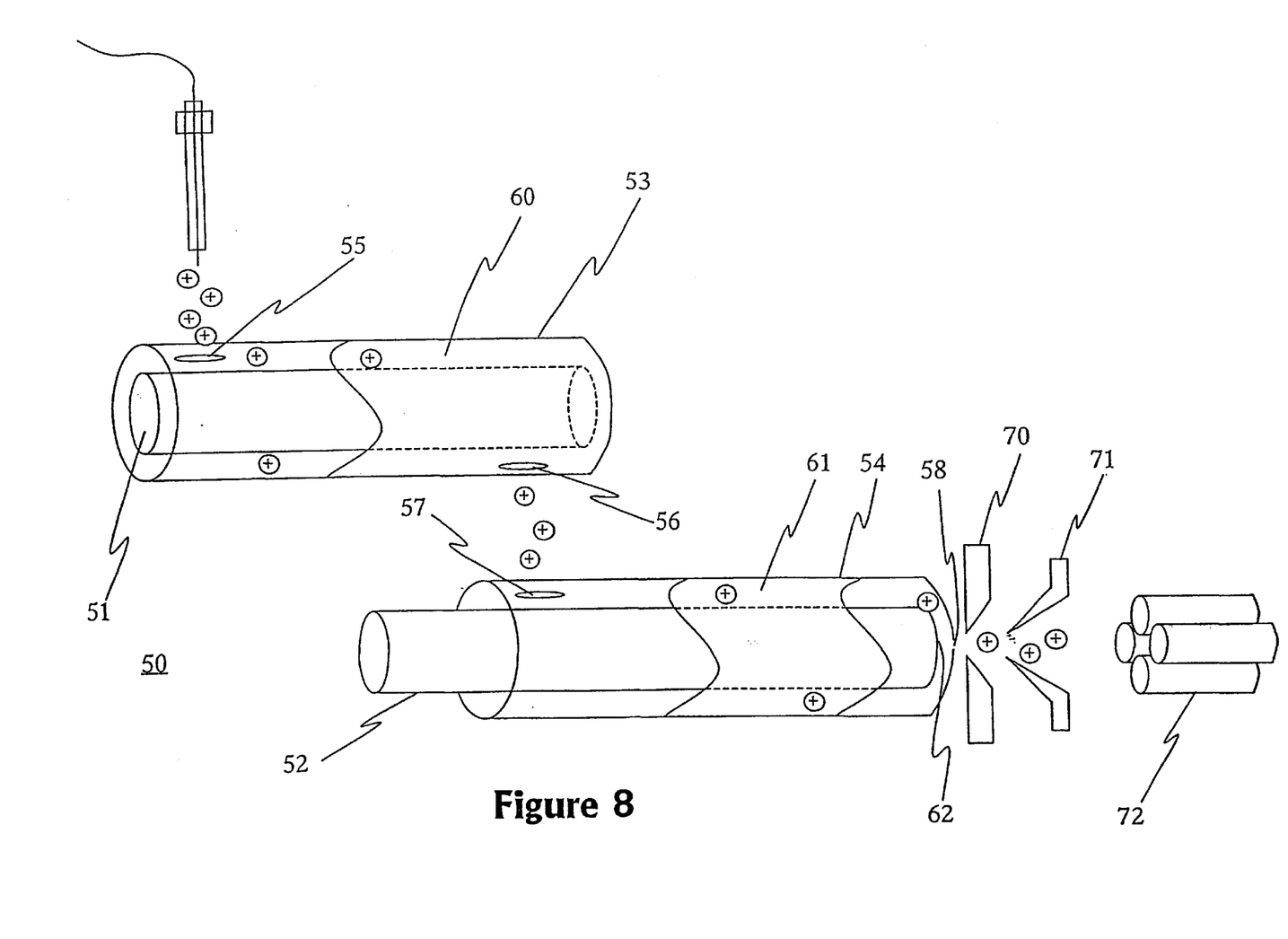
FIG. 8 shows an apparatus according to a third preferred embodiment of the present invention.

Referring to FIG. 8, a tandem FAIMS system composed of two independent FAIMS, each FAIMS having a separate inner cylindrical electrode 51 and 52 and a separate outer cylindrical electrode 53 and 54, according to a third preferred embodiment of the present invention is shown generally at 50. The ions enter an orifice 55 in the first FAIMS and are separated in the analyzer region 60 and pass out of the FAIMS through orifice 56. An orifice 57, which optionally is one and a same as orifice 56, in the outer FAIMS electrode 54 permits ions to enter the analyzer region 61. Those ions that pass through analyzer region 61 exit FAIMS through an orifice 58, which is on the central axis of the outer electrode 54, and adjacent to the spherically domed terminus 62 of the inner FAIMS electrode 52. The ions passing out of the orifice 58 are optionally detected by mass spectrometry after passing through a differentially pumped interface composed of an orifice plate 70 and a skimmer cone 71. The ions are separated in a quadrupole mass analyzer 72 and detected by an ion multiplier (not shown). Other types of interfaces between high pressure, for instance atmospheric pressure, and vacuum are known and are suitable. Other types of mass spectrometers are known, and are optionally used in this system.

Figure 9:
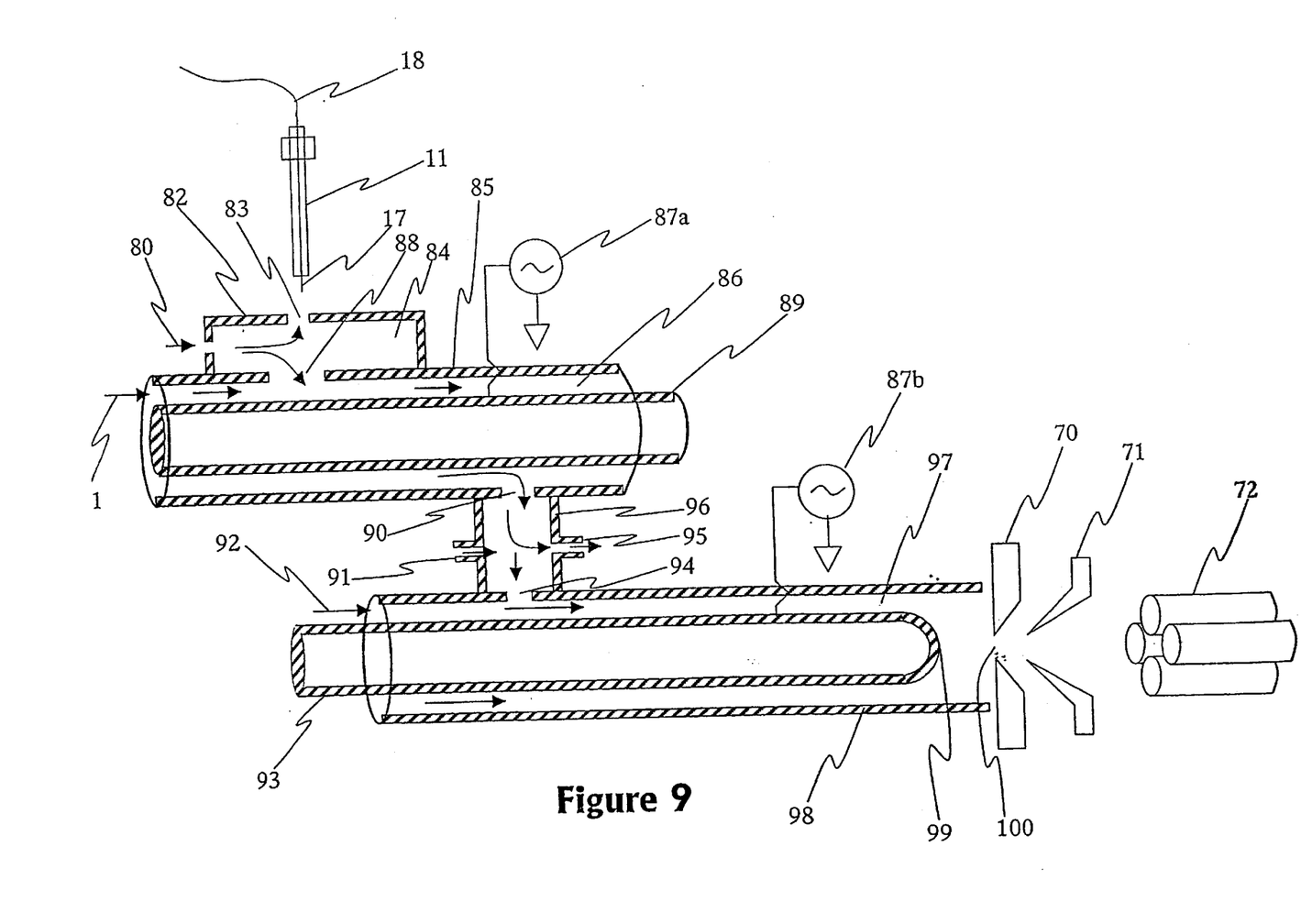
FIG. 9 shows an apparatus according to a fourth preferred embodiment of the present invention.

Referring to FIG. 9, a fourth preferred embodiment of a tandem FAIMS system, composed of two independent FAIMS having a gas flow chamber 96 disposed therebetween, is shown. Each FAIMS has a separate inner cylindrical electrode 89 and 93 and a separate outer electrode 85 and 98, respectively. The gas flow chamber 96 is for adding or removing gases in the region between the tandem FAIMS devices. The ions are produced, for example, using an electrospray ionization source with a liquid delivery capillary 18 and an electrospray needle 11 with a fine tip 17 that is held at high voltage (power supply not shown). The ions pass into FAIMS through a curtain gas assembly composed of a curtain plate 82 with an orifice 83, a gap 84 between the curtain plate 82 and the outer electrode 85 of the first FAIMS, and an orifice 88 in the outer FAIMS electrode 85. A curtain gas 80 enters the gap 84, and escapes in part out through the orifice 83 in the curtain plate 82, and in part travels into the FAIMS analyzer region 86 through the orifice 88. A high voltage asymmetric waveform and a low voltage dc compensation voltage is generated by power supply 87*a* and is applied to the inner cylindrical FAIMS electrode 89, which passes through the central longitudinal axis of the outer FAIMS electrode 85. The fields generated by the voltages applied to the electrode 89 are responsible for the ion separation and ion focusing that takes place in the analyzer region 86.

Referring still to FIG. 9, the ions enter an orifice 88 in the first FAIMS, are separated in the analyzer region 86 and resulting selectively transmitted ions pass out of the first FAIMS through orifice 90. An orifice 94 in the outer FAIMS electrode 98 of the second FAIMS apparatus permits ions to enter the analyzer region 97. A high voltage asymmetric waveform and a low voltage de compensation voltage is generated by power supply 87*b* and is applied to the inner cylindrical FAIMS electrode 93, which passes through the central longitudinal axis of the outer FAIMS electrode 98. The fields generated by the voltages applied to the electrode 93 are responsible for the ion separation and ion focusing that takes place in the analyzer region 97. Those ions that pass through analyzer region 97 exit FAIMS through an orifice 100, which is on the central axis of the outer electrode 98, and adjacent to the spherically domed terminus 99 of the inner FAIMS electrode 93. The ions passing through the orifice 100 in the orifice plate 70 are optionally be detected by mass spectrometry after passing through a differentially pumped interface composed of an orifice plate 70 and a skimmer cone 71. The ions are analyzed subsequently in a quadrupole mass analyzer 72.

As shown in FIG. 9, a gas cell 96 is composed of a gas inlet 91 and a gas outlet 95, through which gas flows. The ions flowing out of orifice 90 from the first FAIMS traverse this cell under the influence of an electric field generated by a voltage difference between the outer FAIMS electrode 85 of the first FAIMS and the outer FAIMS electrode 98 of the second FAIMS. Other optional ion focusing elements assist to create the electric field that assists the ions to traverse gas cell 96. The extraction of ions out of the first FAIMS is accomplished by adjusting the bias voltage applied to the second FAIMS. For example, with positively charged ions, the second FAIMS is operated at −100 volts relative to the first, in order to extract ions from the first, and transport them across to the second FAIMS. If gas phase reactions are required, a closed chamber 96 with gas inlet 91 and gas outlet 95 for gas flows is optionally provided, as is shown in FIG. 9. If this reaction chamber is other than necessary, the two FAIMS units are preferably in very close proximity in order to minimize ion loss in the transfer between these two units.

It is an advantage of the tandem FAIMS/ion-trapping FAIMS apparatus, described previously with reference to FIGS. 7, 8 and 9, that the number of background ions that enters the vacuum system of the optional mass spectrometer detector is minimized, and thus the relative number of analyte ions is maximized. This is achieved by setting the dispersion voltage, and compensation voltages of FAIMS to selectively transmit the compound of interest. Of course, this first advantage is also realized, at least to a partial extent, using either one of the first and the second FAIMS alone as an interface to a mass spectrometer. There are some cases, however, in which other ions, possibly including the background ions, share similar mobility properties with the analyte ions, such that ion separation using a single FAIMS is other than possible.

It is a further advantage of the tandem FAIMS/ion-trapping FAIMS apparatus, described previously with reference to FIGS. 7, 8 and 9, that the waveforms and voltages to control DV and CV within the first analyzer region and within the second analyzer region are independently variable. As such, a first electric field is produced within the first analyzer region for selectively transmitting a first species of ion and a second different electric field is produced within the second analyzer region for selectively transmitting at least one of the first species of ion and a chemically modified derivative of the first species of ion. For instance, it is easy to envision a case in which the background ions are rejected within the first FAIMS analyzer region, and two or more conformers of a same ion are selectively transmitted to the second, ion-trapping FAIMS. Only one conformer is of biological interest, however, so conditions are set within the second FARMS analyzer region to reject the conformer that is other than of biological interest, such that only the conformer of biological interest is trapped. Of course, only those analyte ions that are of interest are trapped, all other ions being rejected within one of the first analyzer region and the second analyzer region, such that the storage period of the second FAIMS is extended in order to accumulate a larger number of ions for transfer to the mass spectrometer. This is completely analogous to the additional and unforeseen advantage that was described previously for the FAIMS-ITMS apparatus.

Yet a further advantage of the tandem FAIMS/ion-trapping FAIMS embodiments of the present invention is that the carrier gas supplied to the second FAIMS is optionally a different gas than the carrier gas supplied to the first FAIMS. Advantageously, a change of carrier gas composition will on some occasions change the high field behavior of an ion significantly, which permits an additional separation to be performed in the second FAIMS analyzer region that cannot be performed in the first FAIMS analyzer region by varying the applied voltages alone. This advantage gives the tandem FAIMS/ion-trapping FAIMS very high compound specificity and resolution.

It is yet a further advantage of the tandem FAIMS/ion-trapping FAIMS apparatus, described previously with reference to FIGS. 8 and 9, that the diameters of the inner and outer electrodes that define a first analyzer region are optionally of different size than the diameters of the inner and outer electrodes that define the second analyzer region. For instance, one particularly useful embodiment employs relatively large diameter electrodes within the first analyzer region for performing a first high resolution ion separation, and relatively small diameter electrodes within the second analyzer region for producing optimized trapping fields near the curved terminus of the inner electrode.

Of course, numerous other embodiments could be envisioned, without departing significantly from the teachings of the present invention.

What is claimed is:

1. A method for trapping ions comprising the steps of:
   a) providing a first analyzer region defined by a space between first and second spaced apart electrodes, the first analyzer region being in communication with a first ion inlet and a first ion outlet, the first ion inlet for receiving ions for introduction into the first analyzer region, the first ion outlet for providing ions from the first analyzer region;
   b) providing a first asymmetric waveform and a first direct-current compensation voltage, to at least one of the first and second electrodes, to form an electric field therebetween, the first asymmetric waveform for effecting a difference in net displacement between the ions in the time of one cycle of the applied first asymmetric waveform;

c) setting the first compensation voltage for effecting a first separation of the ions to selectively transmit a first subset of the ions within the first analyzer region;

d) providing ions to the first analyzer region;

e) coupling ions from the ion outlet of the first analyzer region to a second analyzer; and, f) trapping a selectively transmitted second subset of the ions with the second analyzer to accumulate ions within a trapping region thereof.

2. A method according to claim 1 including the step of: providing a flow of at least a first carrier gas through the first analyzer region for transporting the ions therethrough.

3. A method according to claim 2 wherein the second analyzer comprises a FAIMS analyzer defined by a space between at least two spaced apart electrodes.

4. A method according to claim 3 comprising the step of: providing conditions within the second analyzer for effecting a second separation of ions therein, to support selective transmission of the second subset of the ions within the second analyzer.

5. A method according to claim 4 wherein the step of providing conditions within the second analyzer comprises the step of: providing a second different carrier gas within the second analyzer, the second different carrier gas having a second different predetermined composition than the first carrier gas.

6. A method according to claim 5 wherein the second different carrier gas includes the first carrier gas and at least one additional gaseous component other than the first subset of the ions.

7. A method according to claim 4 wherein the step of providing conditions within the second analyzer comprises the steps of:

providing a second asymmetric waveform and a second direct-current compensation voltage, to at least one of the two electrodes of the second analyzer, to form an electric field therebetween, the second asymmetric waveform for effecting a difference in net displacement between the ions in the time of one cycle of the applied second asymmetric waveform; and, setting the second compensation voltage for effecting the second separation of the ions to selectively transmit the second subset of the ions within the second analyzer.

8. A method according to claim 7 comprising the steps of:

providing a gas flow within the second analyzer; and, adjusting the gas flow within the second analyzer so as to trap the selectively transmitted second subset of the ions within and proximate the trapping region of the second analyzer.

9. A method according to claim 8 comprising the step of applying an extraction voltage at the second ion outlet for extracting the accumulated ions from the trapping region of the second analyzer.

10. A method according to claim 7 wherein the second asymmetric waveform is a different asymmetric waveform than the first asymmetric waveform.

11. A method according to claim 1 comprising the step of: providing conditions within the second analyzer for effecting a second separation of ions therein, to support selective transmission of the second subset of the ions within the second analyzer.

12. A method according to claim 11 wherein the second analyzer comprises a FAIMS analyzer defined by a space between at least two spaced apart electrodes and wherein the step of providing conditions comprises the steps of:

providing a second asymmetric waveform for effecting a difference in net displacement between the ions in the time of one cycle of the applied second asymmetric waveform and a second direct-current compensation voltage to at least an electrode of the second analyzer to form an electric field; and, setting the second compensation voltage for effecting the second separation of the ions to support selective transmission of the second subset of the ions within the second analyzer.

13. A method according to claim 12 comprising the steps of: providing a gas flow within the second analyzer and adjusting the gas flow within the second analyzer so as to trap the selectively transmitted second subset of the ions within and near a three-dimensional region of space within or proximate the trapping region of the second analyzer.

14. A method according to claim 13 comprising the step of: accumulating the selectively transmitted ions within the three-dimensional region during a period of time.

15. A method according to claim 13 comprising the additional step of applying an extraction voltage within or proximate the second analyzer for extracting the accumulated ions from the trapping region of the second analyzer.

16. A method according to claim 11 wherein the second analyzer is an ion trapping mass spectrometer including a ring electrode and a first and a second end-cap electrode.

17. A method according to claim 16 wherein the step of providing conditions within the second analyzer comprises the steps of:

applying at least one of a symmetric radio-frequency potential and a direct-current potential across the ring electrode and the first and second end-cap electrodes, for trapping the first subset of the ions within a three-dimensional region of space within or proximate the second analyzer; and, varying the direct-current potential for effecting the second separation of the ions to selectively trap the second subset of the ions within or proximate the second analyzer.

18. A method according to claim 11 wherein the second analyzer is an analyzer selected from a radio frequency quadrupole ion trap, an FT ion cyclotron resonance mass spectrometer, and a penning trap.

19. A method according to claim 7 comprising the steps of:

providing a gas cell between the first analyzer and the second analyzer, the gas cell having an ion inlet and an ion outlet, the ion inlet for receiving ions from the first analyzer and the ion outlet for providing ions to the second analyzer, the gas cell having a gas inlet and a gas outlet for providing a gas flow through the gas cell and out the gas outlet; and, providing at least a gas within the gas cell for interacting with the ions flowing therethrough.

20. A method according to claim 19 wherein the gas is selected from a group including: a gas for reacting chemically with the ions; a collision gas for inducing fragmentation of the ions; a gas for desolvating the ions; and, a gas for forming at least a complex with the ions in the gas phase.

21. An apparatus for trapping ions comprising:

a) a first analyzer comprising two spaced apart electrodes defining a first analyzer region therebetween, the first analyzer region having a first ion inlet for receiving ions including a first ionic species and a second ionic species for introduction into the first analyzer region and a first ion outlet for providing ions from the first analyzer region;

b) a second analyzer in fluid communication with the first analyzer and disposed for coupling ions provided therefrom, the second analyzer comprising two spaced apart electrodes defining a second analyzer region therebetween, the second analyzer region in communication with a second ion inlet for receiving ions from the first analyzer region for introduction into the second analyzer region, and a second ion outlet for providing ions from the second analyzer region;

c) a first voltage source for providing a first asymmetric waveform and a first direct-current compensation voltage to at least one of the two spaced apart electrodes of the first analyzer, to form a first electric field therebetween, the first electric field for, in use, effecting a difference in net displacement between the ions in the time of one cycle of the applied first asymmetric waveform and the first compensation voltage for, use, effecting a first separation of the ions by supporting selective transmission of a first subset of the ions within the first analyzer region; and, d) a second voltage source for providing at least a temporally varying voltage to at least one of the two electrodes of the second analyzer, to form an electric field therebetween, the field for in use trapping ions within the second analyzer region;

wherein the second analyzer traps more ions of a first ionic species relative to ions of a second ionic species compared to a similar system having only the second analyzer.

22. An apparatus according to claim 21 wherein the second analyzer is a FAIMS analyzer capable of operating in a mode of operation for selectively trapping ions.

23. An apparatus according to claim 22 wherein the two electrodes of the second analyzer comprise outer and inner generally cylindrical coaxially aligned electrode bodies defining a generally annular space therebetween, the annular space forming the second analyzer region.

24. An apparatus according to claim 23 wherein the inner generally cylindrical electrode body of the second analyzer is provided with a terminus shaped for directing the ions generally radially inwardly toward a central longitudinal axis of the inner electrode.

25. An apparatus according to claim 24 the terminus has a smoothly curved surface.

26. An apparatus according to claim 23 wherein one of the two electrodes of the first analyzer is a same electrode as one of the two electrodes of the second analyzer.

27. An apparatus according to claim 21 comprising a gas cell disposed between the first analyzer and the second analyzer, the gas cell in communication with an ion inlet for receiving ions from the first analyzer and an ion outlet for providing ions to the second analyzer, the gas cell in communication with a gas inlet and a gas outlet for providing a gas flow through the gas cell and out the gas outlet.

28. An apparatus according to claim 21 wherein the second analyzer is a mass spectrometer for selectively trapping ions.

29. An apparatus according to claim 21 wherein the second analyzer is selected from a group including: a radio frequency ion trap mass spectrometer, a Fourier transform ion cyclotron resonance mass spectrometer, and a Penning trap.

30. An apparatus for trapping ions comprising:

a first analyzer comprising two spaced apart electrodes defining a first analyzer region therebetween, the first analyzer region having a first ion inlet for receiving ions including a first ionic species and a second ionic species for introduction into the first analyzer region and a first ion outlet for providing ions from the first analyzer region; an electrical controller for providing an asymmetric waveform and a direct-current compensation voltage to at least one of the two spaced apart electrodes of the first analyzer, to form an electric field therebetween, the electric field for, in use, effecting a difference in net displacement between the ions in the time of one cycle of the applied first asymmetric waveform and the first compensation voltage for, in use, effecting a first separation of the ions by supporting selective transmission of a subset of the ions within the first analyzer region;

a second analyzer in fluid communication with the first analyzer region for trapping ions received from the first analyzer region, wherein the second analyzer traps more ions of a first ionic species relative to ions of a second ionic species compared to a similar system having only the second analyzer.

31. An apparatus according to claim 30 wherein the second analyzer is a FAIMS analyzer capable of operating in a mode of operation for selectively trapping ions.

32. An apparatus according to claim 31 wherein the second analyzer comprises outer and inner generally cylindrical coaxially aligned electrode bodies defining a generally annular space therebetween, the annular space defining a second analyzer region.

33. An apparatus according to claim 32 wherein the inner generally cylindrical electrode body of the second analyzer is provided with a terminus shaped for directing the ions generally radially inwardly toward a central longitudinal axis of the inner electrode.

34. An apparatus according to claim 33 wherein the terminus has a smoothly curved surface.

35. An apparatus according to claim 30 wherein the second analyzer is a mass spectrometer for selectively trapping ions.

36. An apparatus according to claim 30 wherein the second analyzer is selected from a group including: a radio frequency ion trap mass spectrometer, a Fourier transform ion cyclotron resonance mass spectrometer, and a Penning trap.

* * * * *

UNITED STATES PATENT AND TRADEMARK OFFICE
CERTIFICATE OF CORRECTION

PATENT NO. : 6,703,609 B2
DATED : March 9, 2004
INVENTOR(S) : Guevremont et al.

It is certified that error appears in the above-identified patent and that said Letters Patent is hereby corrected as shown below:

<u>Column 18,</u>
Line 44, "according to claim 7" should read -- according to claim 1 --

<u>Column 19,</u>
Line 17, "voltage for, use," should read -- voltage for, in use --

Signed and Sealed this

Twelfth Day of October, 2004

JON W. DUDAS
*Director of the United States Patent and Trademark Office*